(12) United States Patent
Ma et al.

(10) Patent No.: US 9,840,514 B2
(45) Date of Patent: Dec. 12, 2017

(54) DIANHYDRIDES, POLYIMIDES, METHODS OF MAKING EACH, AND METHODS OF USE

(71) Applicant: King Abdullah University of Science and Technology, Thuwal (SA)

(72) Inventors: Xiaohua Ma, Thuwal (SA); Ingo Pinnau, Thuwal (SA); Bader Ghanem, Thuwal (SA)

(73) Assignee: King Abdullah University of Science and Technology, Thuwal (SA)

( * ) Notice: Subject to any disclaimer, the term of this patent is extended or adjusted under 35 U.S.C. 154(b) by 0 days.

(21) Appl. No.: 14/900,207

(22) PCT Filed: Jul. 2, 2014

(86) PCT No.: PCT/IB2014/001543
§ 371 (c)(1),
(2) Date: Dec. 21, 2015

(87) PCT Pub. No.: WO2015/001422
PCT Pub. Date: Jan. 8, 2015

(65) Prior Publication Data
US 2016/0152630 A1 Jun. 2, 2016

Related U.S. Application Data

(60) Provisional application No. 61/842,104, filed on Jul. 2, 2013.

(51) Int. Cl.
| | | |
|---|---|---|
| *C08G 73/10* | (2006.01) | |
| *C07D 493/10* | (2006.01) | |
| *C07D 487/10* | (2006.01) | |
| *C07D 209/48* | (2006.01) | |
| *C07D 209/66* | (2006.01) | |
| *C07D 307/89* | (2006.01) | |
| *C07D 307/92* | (2006.01) | |
| *B01D 71/64* | (2006.01) | |

(52) U.S. Cl.
CPC ......... *C07D 493/10* (2013.01); *C07D 209/48* (2013.01); *C07D 209/66* (2013.01); *C07D 307/89* (2013.01); *C07D 307/92* (2013.01); *C07D 487/10* (2013.01); *C08G 73/10* (2013.01); *C08G 73/1007* (2013.01); *C08G 73/1067* (2013.01); *C08G 73/1071* (2013.01); *C08G 73/1085* (2013.01); *B01D 71/64* (2013.01)

(58) Field of Classification Search
CPC .......................... B01D 71/64; C08G 73/1085; C08G 73/1067; C08G 73/1071; C08G 73/1042
See application file for complete search history.

(56) References Cited

U.S. PATENT DOCUMENTS 3,856,752 A 12/1974 Bateman et al.

FOREIGN PATENT DOCUMENTS

| CN | 1448421 A | 10/2003 |
|---|---|---|
| CN | 102617587 A | 8/2012 |
| CN | 102707496 A | 10/2012 |
| JP | 3-247623 A | 11/1991 |
| WO | 2012/035328 A1 | 3/2012 |

OTHER PUBLICATIONS

Ghanem et al (High-Performance Membranes from Polyimides with Intrinsic Microporosity, Adv. Mater. 2008, 20, 2766-2771), Oct. 2008.*
USPTO search report, dated Jan. 2017.*
Rogan et al "Synthesis and gas permeation properties of novel spirobisindane-based polyimides of intrinsic microporosity", Polym. Chem., 2013, 4, 3813-3820, published May 17, 2013.*
Hou, Xiao-wei, et al. "Synthesis of New Polyimides Containing Triptycene." Journal of Huaqiao University (Natural Science), vol. 32 No. 5, Sep. 2011, pp. 532-536 (with English abstract).
International Search Report and Written Opinion of Application No. PCT/IB2014/001543 dated Feb. 11, 2015 18 pages.
Eltamany, Elsayed H., and A-Fe Mourad. "Synthesis and Chemical Properties of N, N'-Dihydroxy (2.2) paracyclophane-4, 5, 12, 13-tetracarboxylic Acid Bisimide." ChemInform 19.29 (1988).
Journal of Huaqiao University (Natural Science), vol. 32 No. 5. Sep. 2011.
Walsh, Christopher J., and Braja K. Mandal. "A new class of aromatic dianhydrides for thermostable polyimides." Chemistry of materials 13.8 (2001): 2472-2475.
Morrow, Benjamin J., et al. "A novel profluorescent nitroxide as a sensitive probe for the cellular redox environment." Free Radical Biology and Medicine 49.1 (2010): 67-76.

* cited by examiner

*Primary Examiner* — Gregory Listvoyb
(74) *Attorney, Agent, or Firm* — Billion & Armitage; Benjamin C. Armitage

(57) ABSTRACT

Embodiments of the present disclosure provide for an aromatic dianhydride, a method of making an aromatic dianhydride, an aromatic dianhydride-based polyimide, a method of making an aromatic dianhydride-based polyimide, and the like.

13 Claims, 6 Drawing Sheets

DIANHYDRIDES, POLYIMIDES, METHODS OF MAKING EACH, AND METHODS OF USE

CROSS-REFERENCE TO RELATED APPLICATIONS

This application is the National Stage of International Application No. PCT/IB2014/001543, filed 2 Jul. 2014, which claims the benefit of and priority to U.S. Provisional Application No. 61/842,104, filed on 2 Jul. 2013, having the title "DIANHYDRIDES, POLYMIDES, METHODS OF MAKING EACH, AND METHODS OF USE", the contents of all of which are incorporated by reference as if fully set forth herein.

BACKGROUND

Polyimides are among the most important high-performance glassy polymers that exhibit exceptional thermal, chemical, and mechanical properties. Polyimides have been used in many areas including the aerospace industry, electronic industry, high temperature adhesion, membranes for separation, composite materials, and the like. However, most polyimides exhibit poor processability due to their high melting points and limited solubility in organic solvents. Microporous polyimides have been developed to overcome these deficiencies, however, microporous polyimides are challenging to synthesize due, at least in part, to limitations of suitable reagents.

SUMMARY

Embodiments of the present disclosure provide for an aromatic dianhydride, a method of making an aromatic dianhydride, an aromatic dianhydride-based polyimide, a method of making an aromatic dianhydride-based polyimide, and the like.

In an embodiment, a composition, among others, can include: an aromatic dianhydride having the following structure:

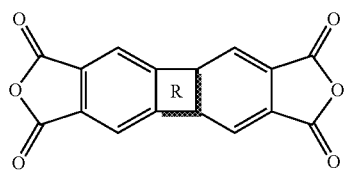

wherein R is selected from the following structures:

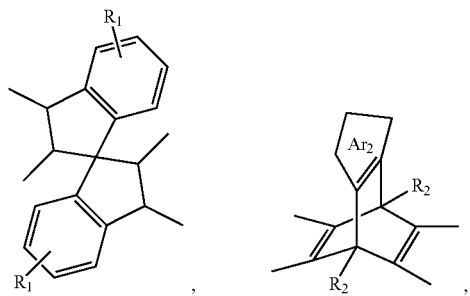

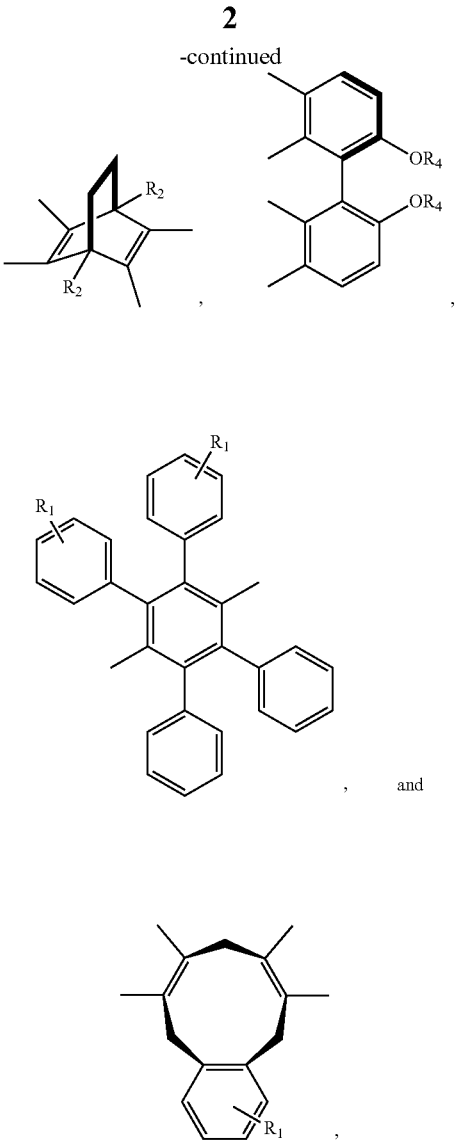

wherein each $R_1$, $R_2$, and $R_4$ are independently selected from the group consisting of: a linear or branched, substituted or unsubstituted, alkyl group, wherein $Ar_2$ is selected from the group consisting of: an aryl group and a heteroaryl group where each are substituted or unsubstituted.

In an embodiment, a composition, among others, can include: a polyimide having the following structure:

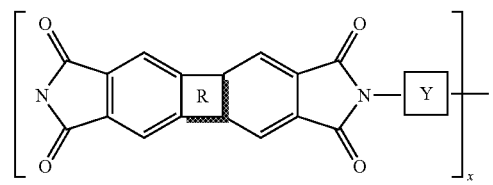

wherein Y is selected from an aryl group or a heteroaryl group, wherein x is 1 to 10,000, wherein R is selected from the following structures:

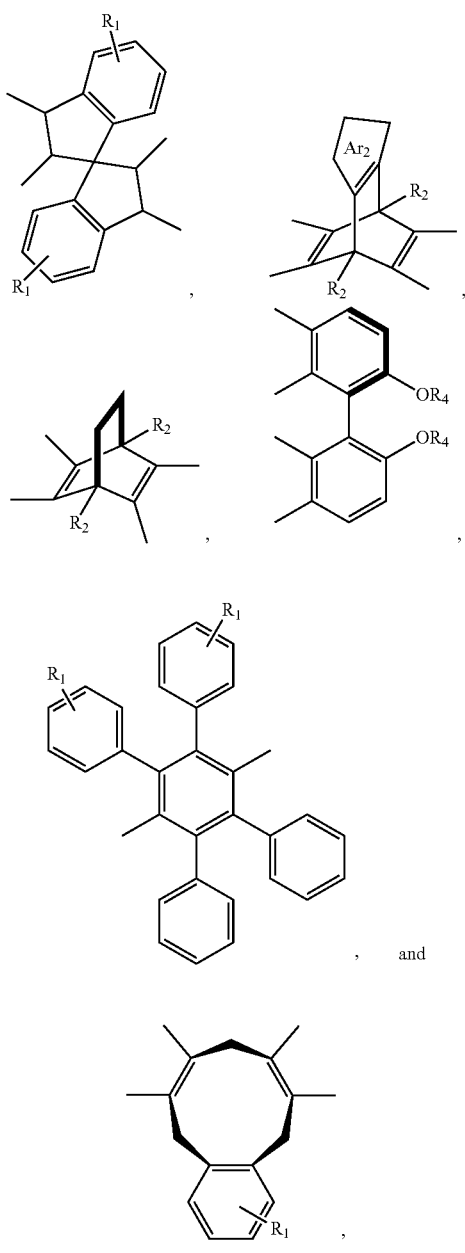

wherein each of $R_1$, $R_2$, and $R_4$ are independently selected from the group consisting of: a linear or branched, substituted or unsubstituted alkyl group, wherein $Ar_2$ is selected from the group consisting of: an aryl group and a heteroaryl group where each can be substituted or unsubstituted.

In an embodiment, a composition, among others, can include: a polyimide having the following structure:

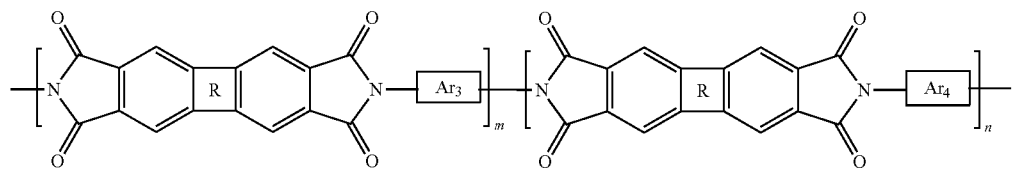

wherein $Ar_3$ and $Ar_4$ are independently selected from an aryl group or a heteroaryl group, wherein m and n are independently 0 or 10,000, wherein R is selected from the following structures:

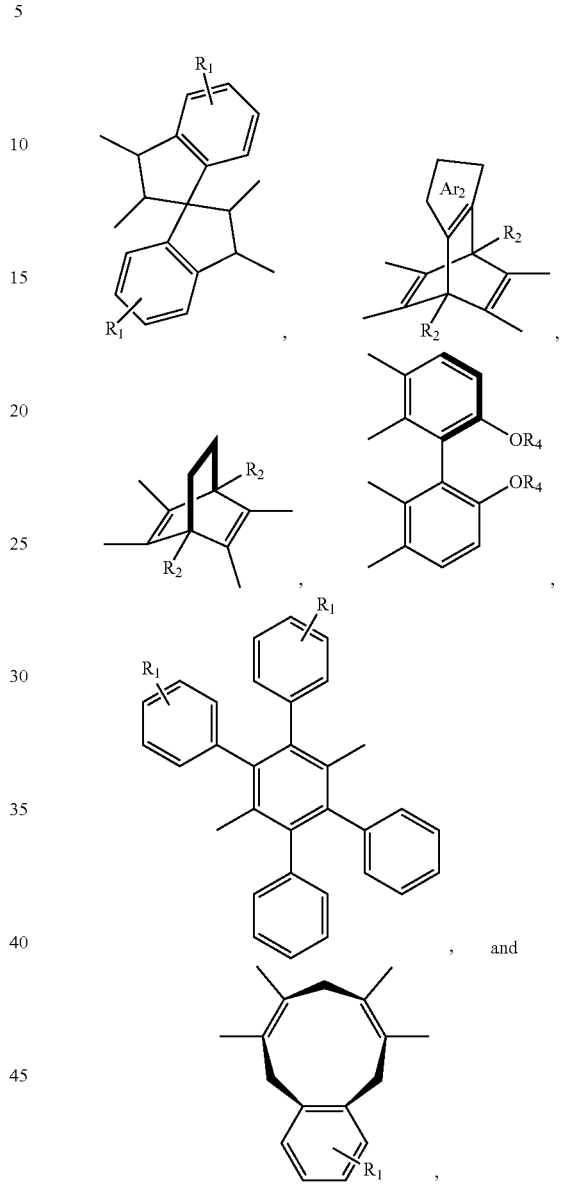

wherein $R_1$, $R_2$, and $R_4$ are independently selected from the group consisting of: a linear or branched, substituted or unsubstituted alkyl group, wherein $Ar_2$ is selected from the group consisting of: an aryl group and a heteroaryl group, wherein $R_5$ is a linear or branched, substituted or unsubstituted alkyl group.

In an embodiment, a method of making an aromatic dianhydride, among others, can include:

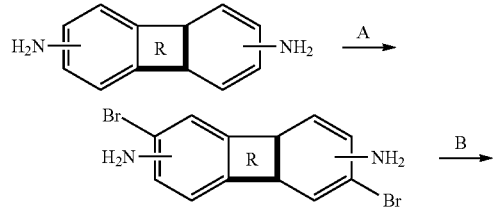

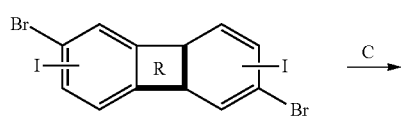

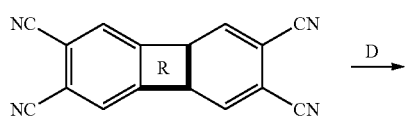

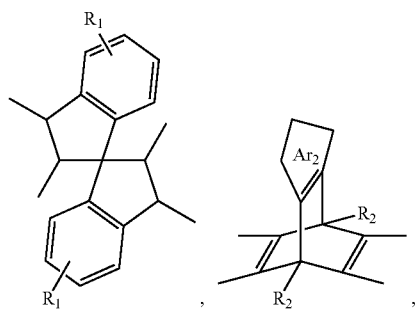

wherein A includes N-bromosuccinimide, wherein B includes sodium nitrite, wherein C includes copper cyanide, wherein D includes potassium hydroxide followed by acetic anhydride, wherein R is selected from the following structures:

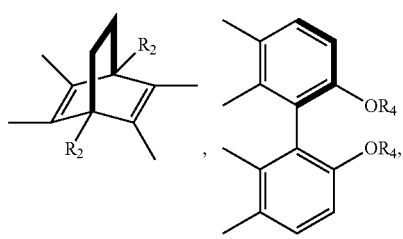

-continued

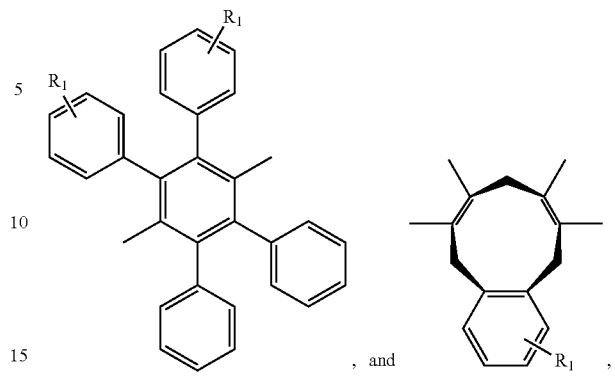

, and wherein $R_1$, $R_2$, and $R_4$ are independently selected from the group consisting of: a linear or branched, substituted or unsubstituted alkyl group, wherein $Ar_2$ is selected from the group consisting of: an aryl group and a heteroaryl group where each is substituted or unsubstituted.

In an embodiment, a method for making a polyimide, among others, can include: reacting an aromatic dianhydride with a multi-amine to form a polyimide or polypyrrolone, wherein the aromatic dianhydride has the following structure:

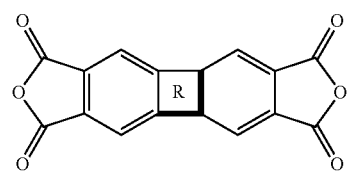

wherein R is selected from the following structures:

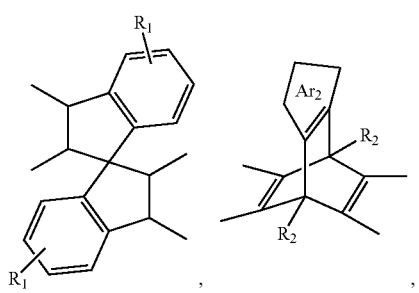

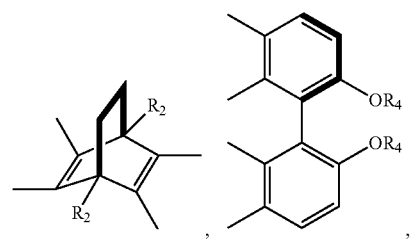

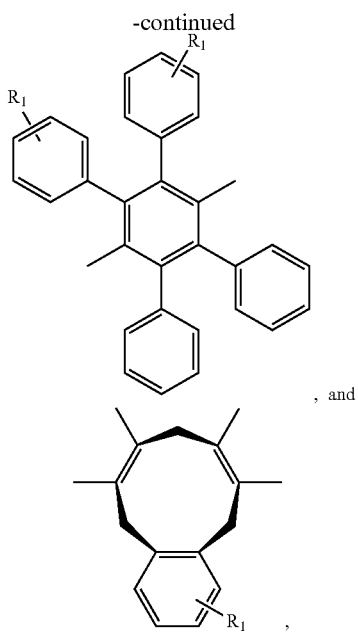

, and wherein each $R_1$, $R_2$, and $R_4$ are independently selected from the group consisting of: a linear or branched, substituted or unsubstituted, alkyl group, wherein $Ar_2$ is selected from the group consisting of: an aryl group and a heteroaryl group where each are substituted or unsubstituted.

BRIEF DESCRIPTION OF THE DRAWINGS

Further aspects of the present disclosure will be more readily appreciated upon review of the detailed description of its various embodiments, described below, when taken in conjunction with the accompanying drawings.

DETAILED DESCRIPTION

Figure 1:
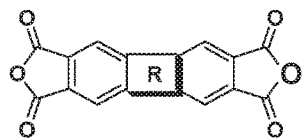
FIG. 1 illustrates an embodiment of an aromatic dianhydride.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, polymer chemistry, analytical chemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar. Standard temperature and pressure are defined as 0° C. and 1 bar.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

The term "substituted" refers to any one or more hydrogens on the designated atom that can be replaced with a selection from the indicated group, provided that the designated atom's normal valence is not exceeded.

As used herein, "aliphatic" or "aliphatic group" refers to a saturated or unsaturated, linear or branched, cyclic (non-aromatic) or heterocyclic (non-aromatic), hydrocarbon or hydrocarbon group and encompasses alkyl, alkenyl, and alkynyl groups, and alkanes, alkene, and alkynes, for example.

As used herein, "cyclic" group refers to a cyclic hydrocarbon having a stable 4, 5, 6, 7, 8, 9, 10, 11, or 12 membered (e.g., carbon or hetero), (unless the number of members is otherwise recited), monocyclic, bicyclic, or tricyclic cyclic ring.

As used herein, "alkyl" or "alkyl group" refers to a branched saturated aliphatic hydrocarbon. Examples of alkyl include, but are not limited to iso-propyl, sec-butyl, t-butyl, and iso-pentyl.

The term "substituted," as in "substituted alkyl", "substituted aryl," "substituted heteroaryl" and the like means that the substituted group may contain in place of one or more hydrogens a group such as alkyl, hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Preferred examples are furanyl, imidazyl, pyranyl, pyrrolyl, and pyridyl.

General Discussion

Embodiments of the present disclosure provide for an aromatic dianhydride, a method of making an aromatic dianhydride, an aromatic dianhydride-based polyimide, a method of making an aromatic dianhydride-based polyimide, and the like. Embodiments of the aromatic dianhydride-based polyimides have one or more of the following characteristics: intrinsic microporosity, good thermal stability, and enhanced solubility. Intrinsic microporosity is defined herein as a polymeric material with pore sizes of less than 2 nm and a surface porosity of >100 m$^2$/g, as determined by the nitrogen adsorption method at 77 K.

Due to their good solubilities, thermal and chemical stabilities, and high microporosities, these materials can be implemented in a wide range of industrial applications related to aerospace industry, electronic industry, high temperature adhesion, membranes for separation, and composite materials.

In an exemplary embodiment, the aromatic dianhydride-based polyimide can be made using an aromatic dianhydride as shown in the following structure:

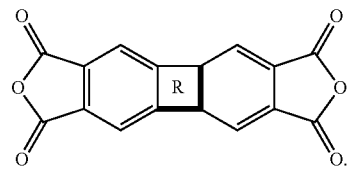

In an embodiment, R can be selected from the following structures, where each structure can be substituted or unsubstituted, bonded via the bonds noted:

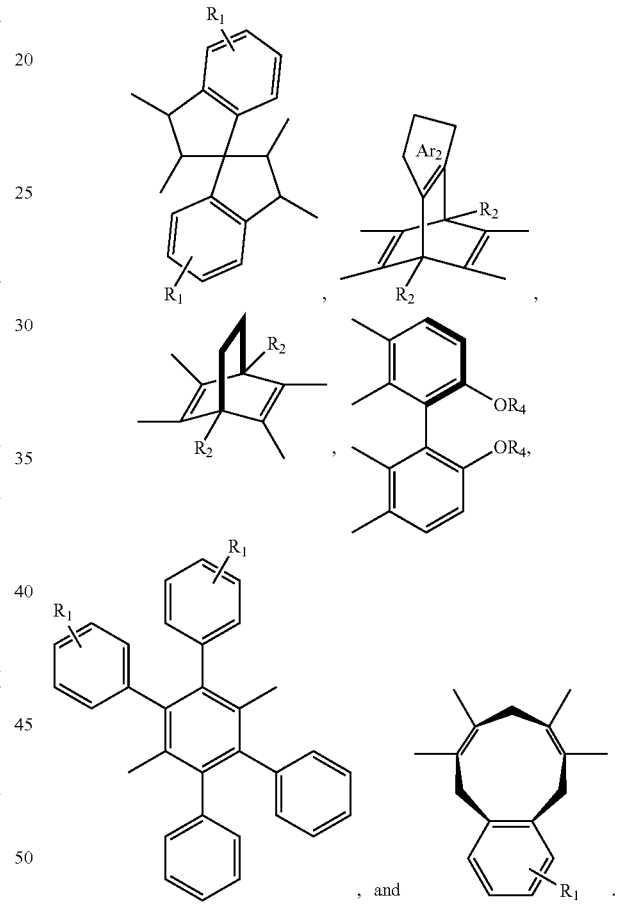

The bonds shown for the R groups noted above are shown in such a way as to show how the anhydride groups are bonded and not to indicate a methyl group. The way in which bonds are formed for the R group to the anhydrides can be better understood by considering the bonding schemes shown in FIG. 1. For example, the bonds shown can be part of the aromatic ring of the formed structure, structure A, B, C, D, and F, or can be attached to a position (not necessarily the position shown) on the aromatic ring, structure E and G.

In an embodiment, each $R_1$, $R_2$, and $R_4$ can be independently selected from: a linear or branched, substituted or unsubstituted alkyl group. In an embodiment, each $R_1$, $R_2$, and $R_4$ can be independently selected from a methyl group, an ethyl group, a propyl group, and a butyl group (linear or branched), each substituted or unsubstituted. The phrase "independently selected from" can mean selection from $R_1$, $R_2$, and $R_4$ independent of one another, or can mean that in each instance of $R_1$ (as well as $R_2$ and $R_4$), each $R_1$ is selected independently of the other $R_1$s (e.g., one $R_1$ can be a methyl group and the other $R_1$ can be a propyl group).

Embodiments where $R_1$ is indicated as attached to a ring (e.g., an aromatic ring), $R_1$ can be attached to any carbon of the ring. Embodiments where $R_1$ is attached to a ring, one, two, or more $R_1$s can be attached to the ring to replace hydrogens on the ring. For example, the ring can have two or more $R_1$s attached to the same ring at the same or different carbons.

In an embodiment, $Ar_2$ can be an aryl group or a heteroaryl group, substituted or unsubstituted. In an embodiment, $Ar_2$ can be selected from:

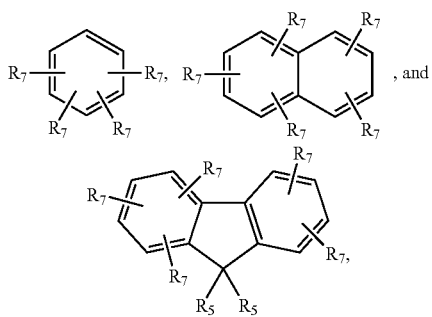

that is bonded by removing a hydrogen from the ring for two carbons and each ring can have up to four $R_7$ groups. In an embodiment, $Ar_2$ can be selected from

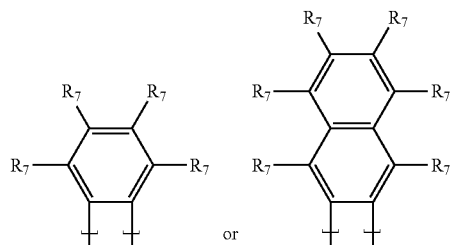

Figure 2:
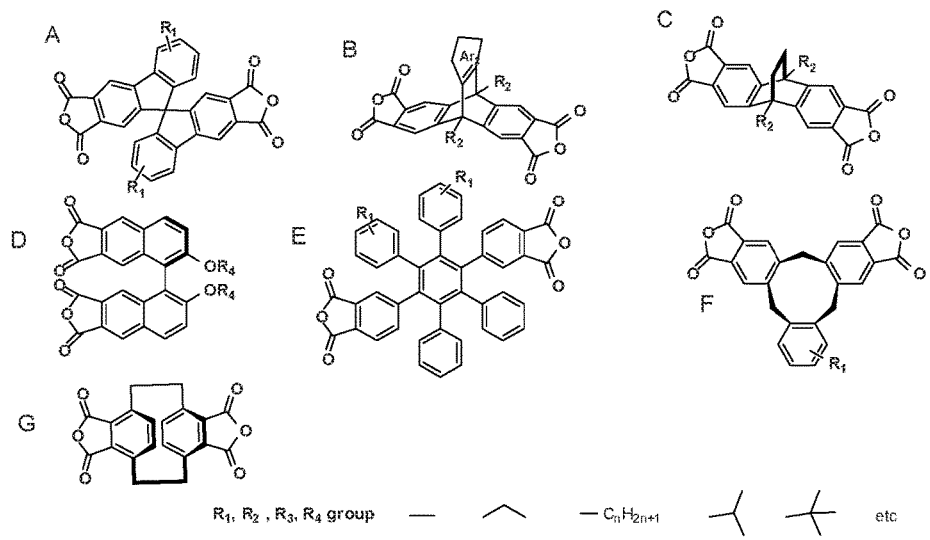
FIG. 2 illustrates embodiments of R.

In an embodiment, each $R_5$ and $R_7$ can be independently a linear or branched, substituted or unsubstituted, alkyl group (e.g., methyl group). Each $R_5$ can be independently selected. Each $R_7$ can be independently selected. Examples of the aromatic dianhydride are shown in FIGS. 1 and 2.

Figure 3:
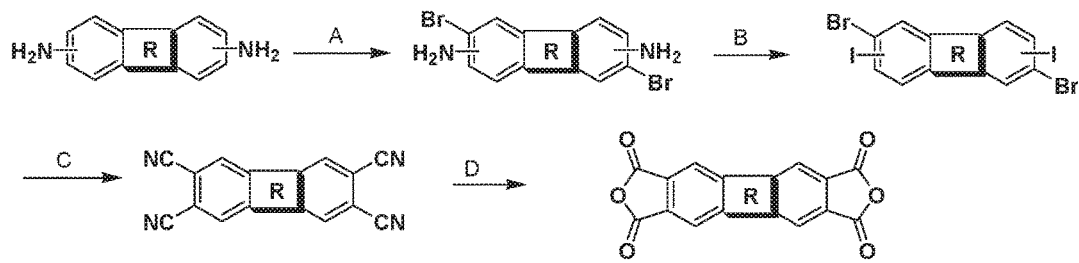
FIG. 3 illustrates an embodiment of making an aromatic dianhydride.
Figure 4:
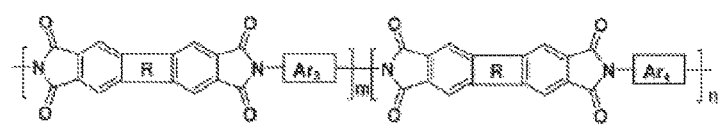
FIG. 4 illustrates an embodiment of an aromatic dianhydride-based polyimide.

In an embodiment, the aromatic dianhydride can be produced using the reaction sequence shown in FIG. 3, where R and the other variables are defined as noted above. In an embodiment, step A includes the bromination of the aromatic diamine at the orth-position. The reaction can take place at room temperature or in an ice-bath, and the reaction time can be about 5 minutes to about 30 minutes, depending on the activity of the diamines. The bromination reagent can be NBS or the bromine element.

In an embodiment, step B includes changing the diamine group of intermediate to diiodo group using a diazonium salt (e.g., sodium nitrite, isopentyl nitrite or some other nitrites). The introduction of the iodo group can be any inorganic salt containing an iodide element such as sodium iodide or potassium iodide. The reaction can be carried out in ice bath in acidic conditions and lasts for about 1 to 2 hrs depending on the activity of the diamines.

In an embodiment, step C can include switching the dibromo-diiodo intermediate to tetracyanate intermediate, which can be carried out by aromatic substitution with CuCN in a highly polar solvent at a high temperature such as about 120° C.

In an embodiment step D can include the hydrolysis of the tetracyanate, in basic conditions. An inorganic base such as potassium hydroxide or sodium hydroxide can be used to form a tetra-acid, which can further undergo cyclic reaction to dianhydride. Acetic anhydride can be used in cyclic reaction.

In an embodiment, the aromatic dianhydride can be used to form aromatic dianhydride-based polyimide homopolymers or co-polymers. In an embodiment, the aromatic dianhydride-based polyimide can have one of the following structures:

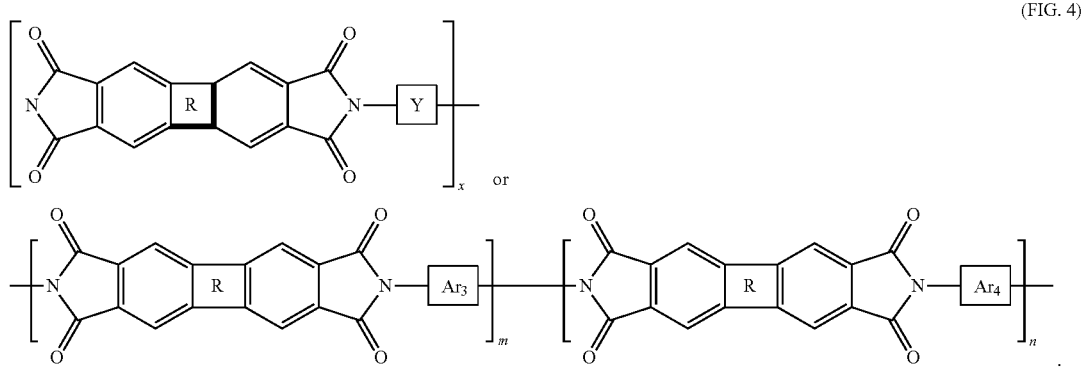

(FIG. 4)

In an embodiment, Y, $Ar_3$, and $Ar_4$, can each independently be an aryl group or heteroaryl group and x can be 1 to 10,000.

In an embodiment, Y can be:

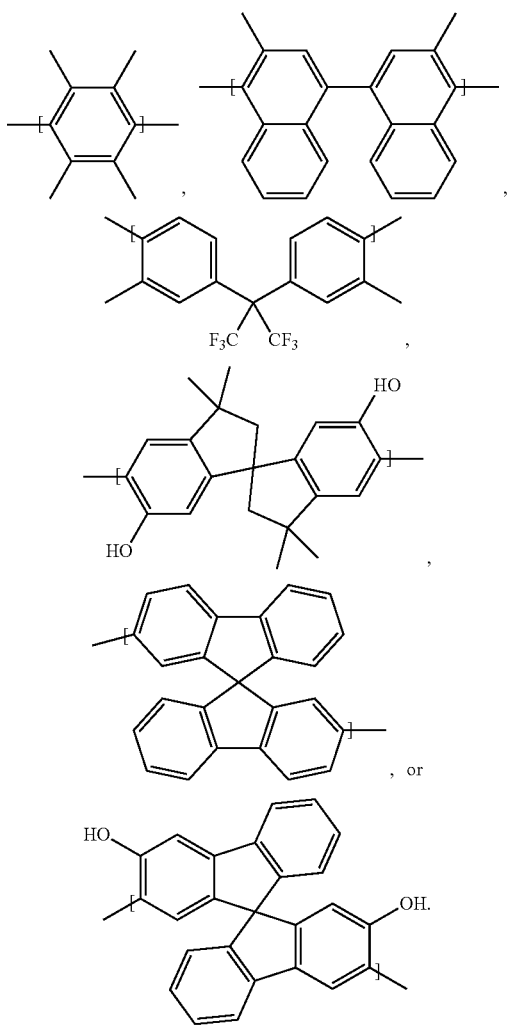

In an embodiment, the Y, $Ar_3$, and $Ar_4$, group can be an aryl group or heteroaryl group that can be derived from the following aromatic diamines: an aryl diamine group or a heteroaryl diamine group. In an embodiment, the aryl diamine group can be:

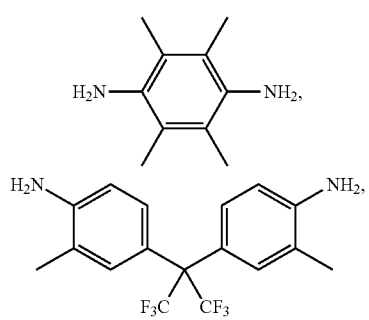

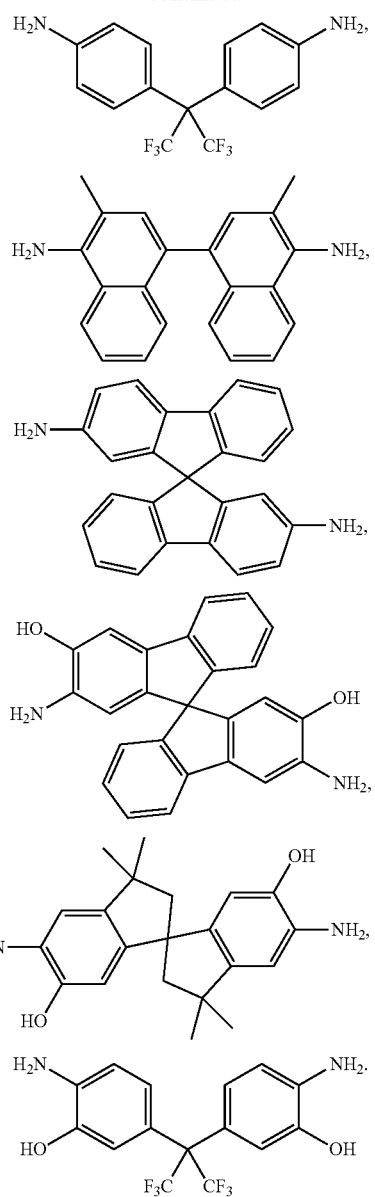

In an embodiment, the Y, $Ar_3$, and $Ar_4$, group can be derived from a heteroaryl diamine group such as

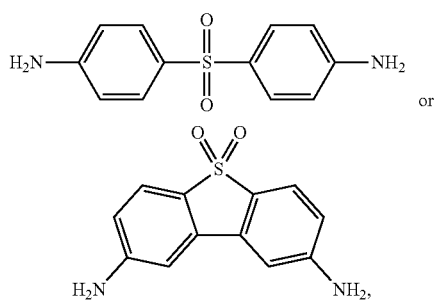

where the Y, $Ar_3$, and $Ar_4$, groups can correspond to:

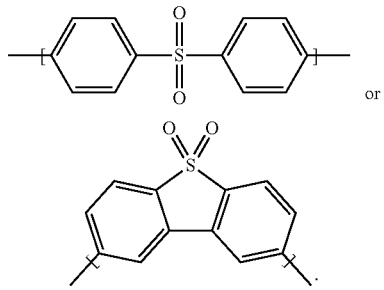

In an embodiment, $Ar_3$ and $Ar_4$ are different. The subscript m and n can be independently 0 to 10,000 or 1 to 10,000. In an embodiment, R can include R as it is defined above.

In an embodiment, an aromatic dianhydride-based polyimide can be formed by the reaction of an aromatic dianhydride with a multi-amine. In general, the aromatic dianhydride is reacted with a multiamine in a solvent (e.g., NMP, DMAc, m-cresol or DMSO under certain conditions via one step heating method or two step method reaction) to form the aromatic dianhydride-based polyimide.

Figure 5:
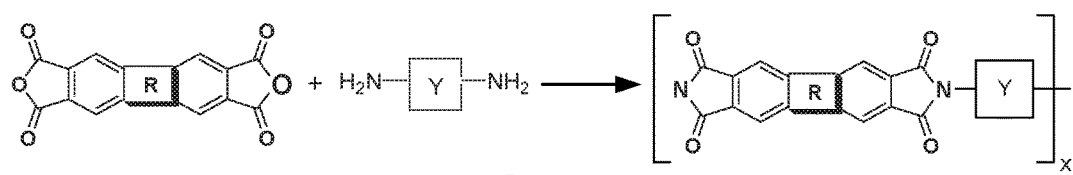
FIG. 5 is an illustrative embodiment illustrating how diamines can be used to form an aromatic dianhydride-based polyimide.
Figure 6:
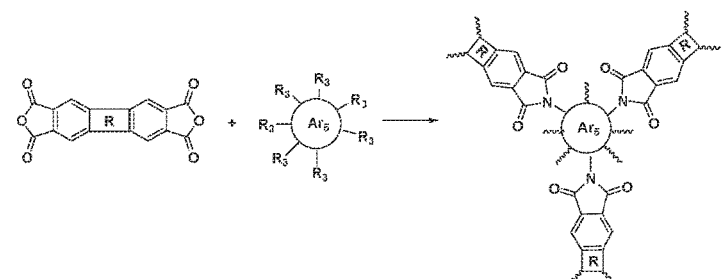
FIG. 6 is an illustrative embodiment illustrating how multiamines can be used to form aromatic dianhydride-based polyimides.

In an embodiment, the multi-amine can be a diamine, triamine, tetramine, or an amine having 5 or more amino groups. Exemplary examples of reactions to form polyimides are shown in FIGS. 5 and 6. The subscript x can be 0 to 10,000 or 1 to 10,000.

FIG. 6 is an illustrative embodiment illustrating how multiamines can be used to form aromatic dianhydride-based polyimides. In regard to FIG. 6, $Ar_5$ can be an aliphatic or aromatic group (e.g., aryl or heteroaryl) having multiple amino groups (represented by $R_3$). However, $Ar_5$ could be designed to have two, three, four, five, or more $R_3$ groups so $Ar_5$ is not limited to the structure shown in FIG. 6. In an embodiment, one or more of the $R_3$ groups can be an amino group, where a diamine, a triamine, a tetramine, or an amine having 5 or more amino groups can be formed.

Exemplary examples of diamine include the following structures:

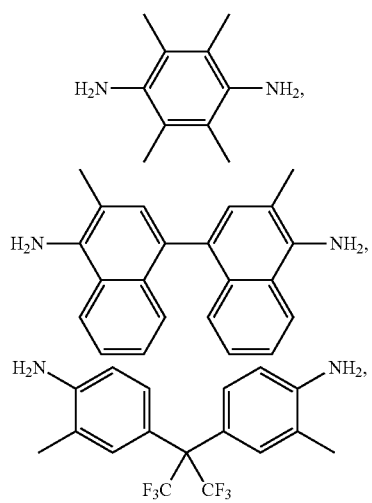

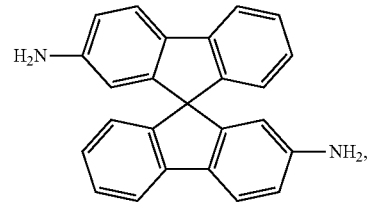

MK-4

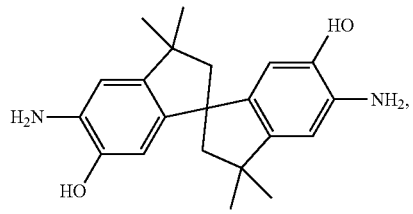

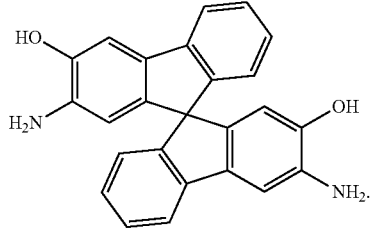

and

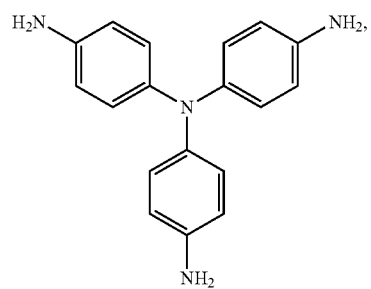

Examples of triamines can include the following structures:

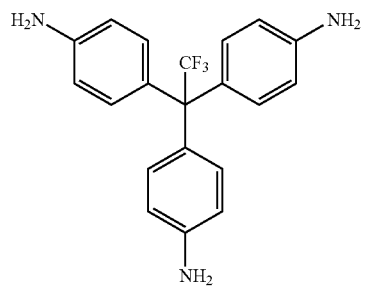

or

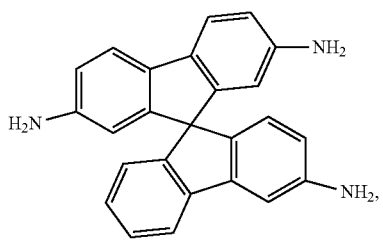

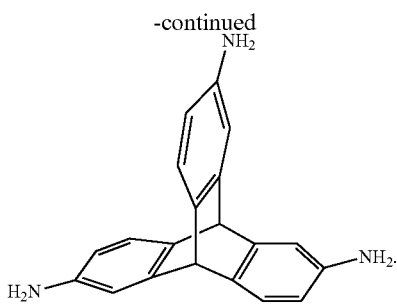

Exemplary examples of tetramines can include the following structures:

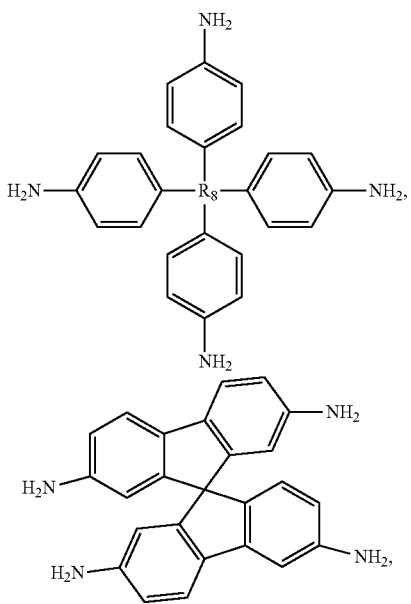

where $R_8$ can be carbon, silicon atom or adamantyl core.

Figure 7:
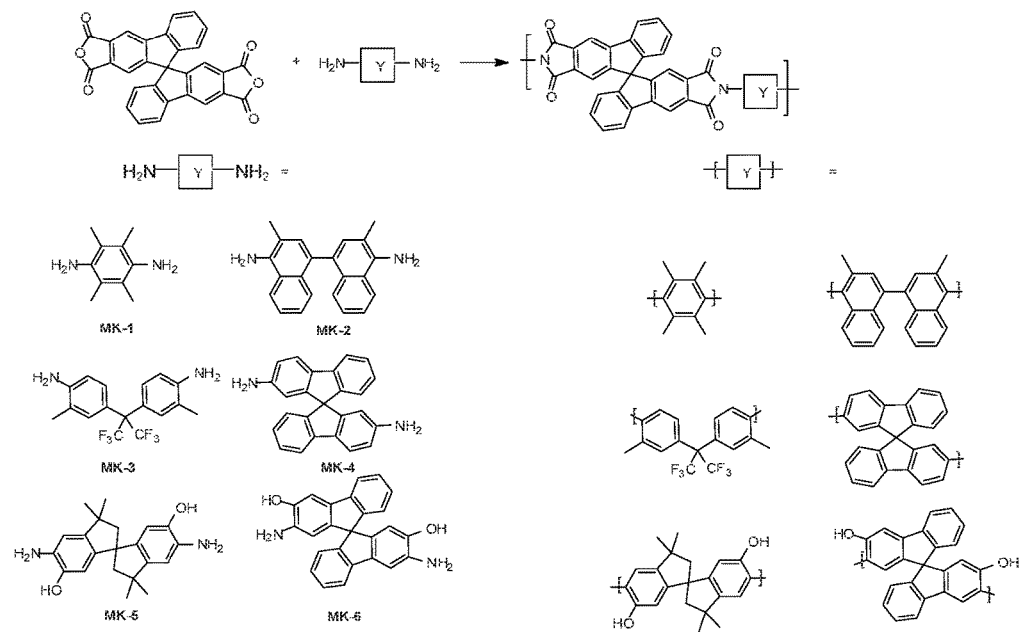
FIG. 7 illustrates a specific embodiment of an aromatic dianhydride-based polyimide can be formed using a specific aromatic dianhydride.
Figure 8A:
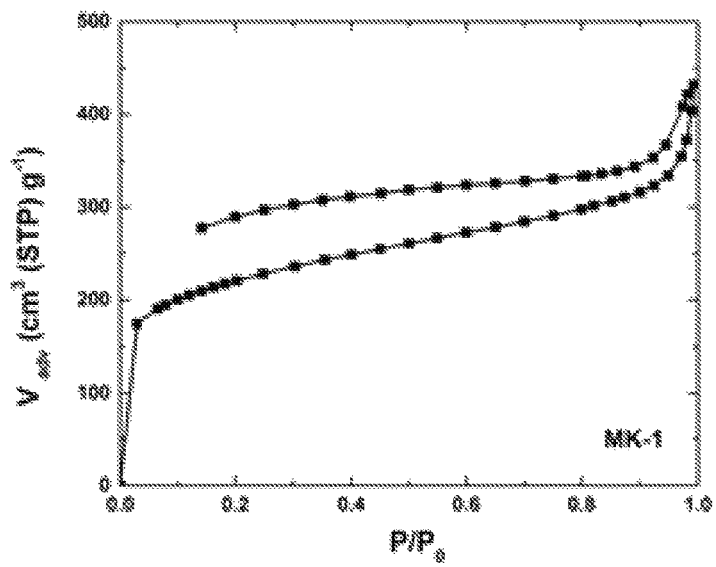
FIGS. 8A-8F illustrates graphs of BET isotherms of some novel polyimides as noted in the Examples.
Figure 8B:
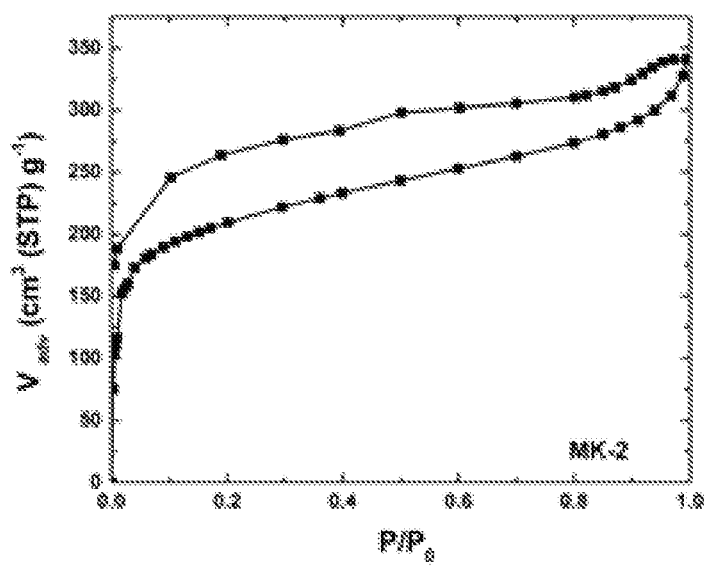
Figure 8C:
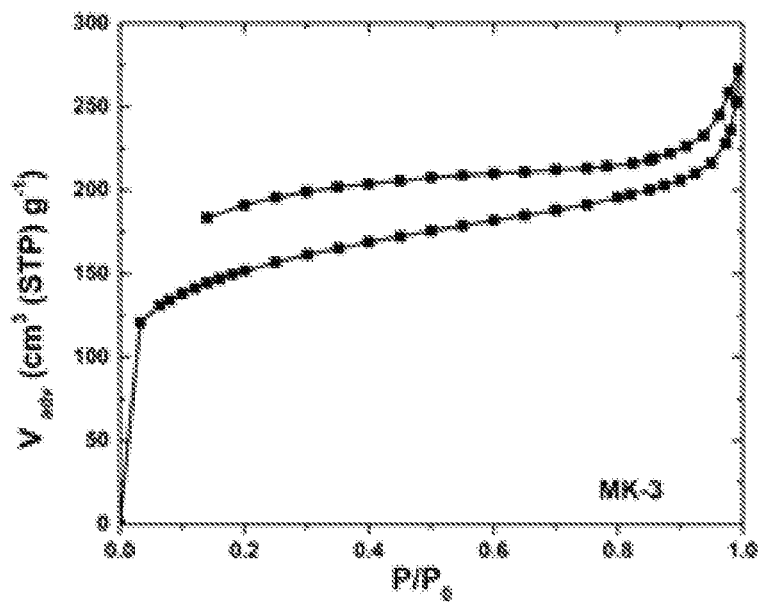
Figure 8D:
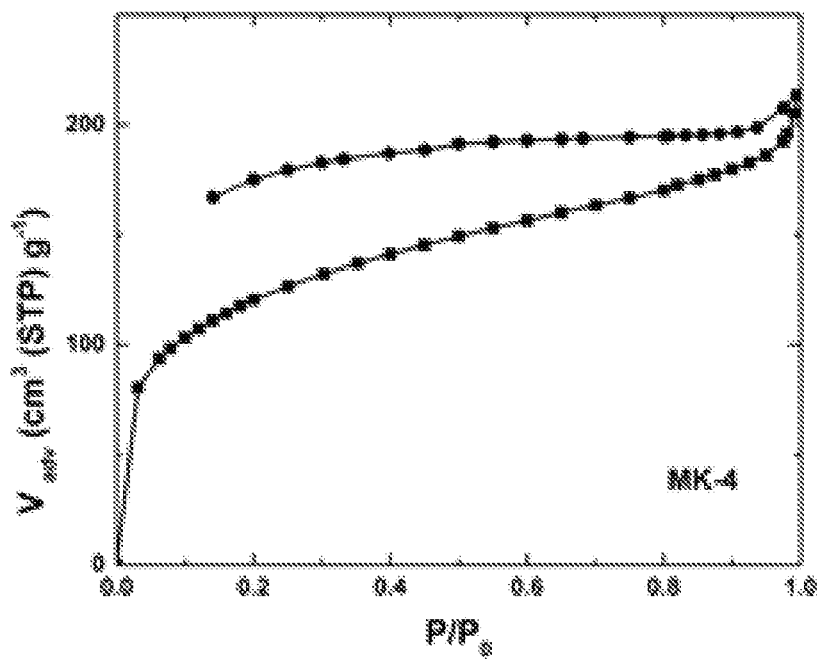
Figure 8E:
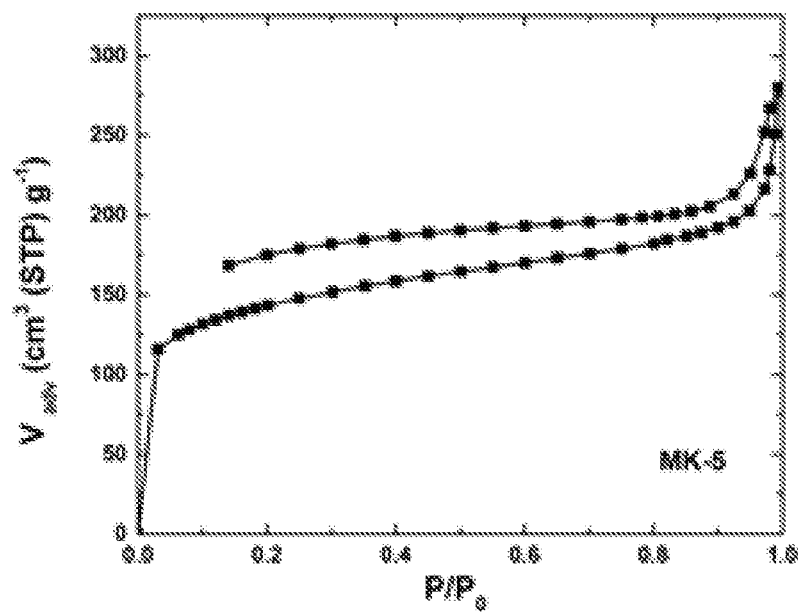
Figure 8F:
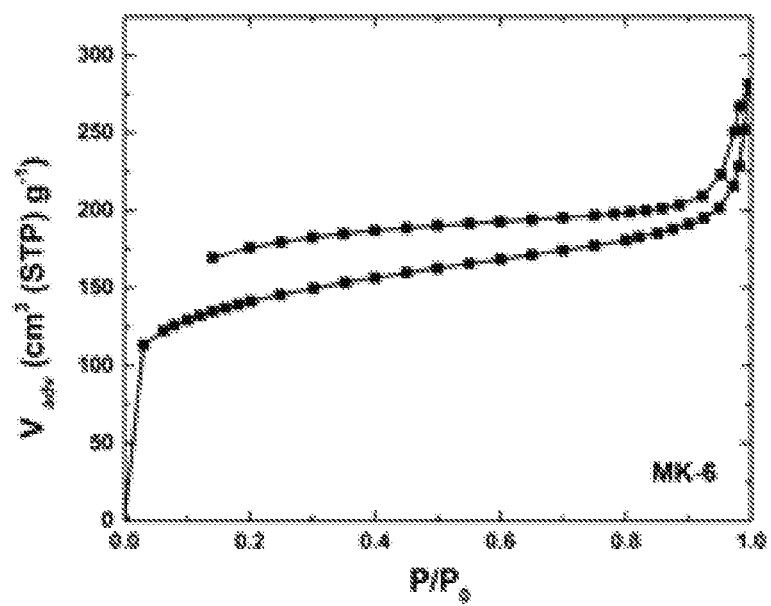

In an embodiment shown in FIG. 7, a specific embodiment of an aromatic dianhydride-based polyimide can be formed using a specific aromatic dianhydride. FIGS. 8A-8F illustrates graphs of BET isotherms of some novel polyimides as noted in the Examples.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Examples of the Monomer Synthesis

Example 1

Synthesis of 2,2',3,3'-tetracarboxyl-9,9'-spirobifluorene 2,2',3,3'-tetracyano-9,9'-spirobifluorene (624 mg, 1.50 mmol) was mixed with a solution of water/ethanol (10 mL/10 mL). Then, KOH (1740 mg, 30 mmol) was slowly added and the mixture was refluxed overnight. After the solution was cooled to room temperature, it was poured into acid (HCl, 6N) to adjust the PH to 1-2. After removal of the ethanol and water, methanol was added again to dissolve the product and filtered to remove the organic phase. Thereafter, THF (20 mL) was added to the solid, filtered, and the THF solution was added dropwise to 300 mL DCM. An off-white solid was obtained after filtration.

Example 2

Synthesis of the 2,2',3,3'-dianhydride-9,9'-spirobifluorene 2,2',3,3'-tetracarboxyl-9,9'-spirobifluorene (1.06 g, 2.15 mmol) was added to $Ac_2O$ (15 mL). The solution was refluxed for 6 hrs and filtered to obtain needle crystals: 0.9 g (yield: 98%). $^1$H NMR (400 MHz, $CDCl_3$): 8.45 (s, 2H), 8.07 (d, 2H, J=7.72 Hz), 7.58 (t, 2H, J=7.48 Hz, 7.50 Hz), 7.36 (t, 2H, J=7.48 Hz, 7.50 Hz), 7.24 (s, 2H), 6.82 (d, 2H, J=7.68 Hz). Anal: calcd for $C_{29}H_{12}O_6$: C, 76.32; H, 2.65. Found: C, 75.42; H, 2.06; HRMS: calcd for $C_{25}H_{18}N_2O_2$: 456.0634. Found: 406.06284.

Example 3

Synthesis of MK-1

2,2',3,3'-dianhydride-9,9'-spirobifluorene (456.06 mg, 1.00 mmol) and 2,3,5,6-tetramentyl,1,4-phenyldiamine (164.13 mg, 1.00 mmol) were added to m-cresol (3 mL). The solution was heated to 60° C. for 1 hr before isoquinoline (5 drops) was added and, thereafter, the system was heated up to 180° C. for 4 hrs. The polymer was precipitated in methanol (100 mL), then dried and dissolved in chloroform and re-precipitated in MeOH. After filtration, the polymer was dried in a vacuum oven overnight and an off-white polymer powder (590 mg, yield 95%) was obtained. $^1$H NMR (400 MHz, $CDCl_3$): 8.43 (s, 2H), 8.02 (s, 2H), 7.53 (s, 2H), 7.31 (s, 2H), 6.88 (s, 2H), 2.06 (s, 12H); Molecular weight (GPC in chloroform) $M_n=9.3\times10^3$; $M_w=1.9\times10^4$; PDI=2.01; BET surface area: 754 $m^2/g$.

Example 4

Synthesis of the MK-2

2,2',3,3'-dianhydride-9,9'-spirobifluorene (456.06, 1.00 mmol) and 3,3'-dimethylnaphthidine (312.42 mg, 1.00 mmol) were added to m-cresol (3 mL). The solution was heated to 60° C. for 1 hr before isoquinoline (5 drops) was added and, thereafter, the system was heated up to 180° C. for 4 hrs. The polymer was precipitated in methanol (100 mL), then dried and dissolved in chloroform and re-precipitated in MeOH. After filtration, the polymer was dried in a vacuum oven overnight and a light yellow polymer powder (730 mg, yield 95%) was obtained. $^1$H NMR (400 MHz, $CDCl_3$): 8.56 (s, 2H), 8.09 (s, 2H), 7.42-7.62 (m, 16H), 6.97 (s, 2H), 2.42 (s, 6H); Molecular weight (GPC in chloroform) $M_n=2.5\times10^4$; $M_w=6.4\times10^4$; PDI=2.67.

Example 5

Synthesis of the MK-3

9,9'-spirobifluorene-2,2'-diamine was adopted, the resulted polyimide (MK-3) was synthesized by the same procedure as MK-1 with a yield of 95%. $^1$H NMR (400 MHz, $CDCl_3$): 8.24 (s, 2H), 7.89 (s, 4H), 7.78 (s, 2H), 7.42 (s, 2H), 7.31-7.35 (m, 4H), 7.18 (s, 2H), 7.09-7.11 (m, 2H), 7.03 (s, 2H), 6.76-6.79 (m, 4H), 6.70 (s, 2H); Molecular weight (GPC in chloroform) $M_n=14.4\times10^4$; $M_w=23.5\times10^4$; PDI=1.63.

Example 6

Synthesis of the MK-4

4,4'-(perfluoropropane-2,2-diyl)bis(2-methylaniline) was used as the starting diamine compound and the resulting polyimide (MK-4) was synthesized by the same procedure as MK-1 with a yield of 95%. $^1$H NMR (400 MHz, CDCl$_3$): 8.40 (d, 2H, J=1.27 Hz), 8.01 (s, 2H), 7.51 (s, 2H), 7.22-7.46 (m, 10H), 6.97 (d, 2H, J=2.0 Hz), 2.18 (s, 6H); Molecular weight (GPC in chloroform) $M_n=7.70\times10^4$; $M_w=13.1\times10^4$; PDI=1.70.

Example 7

Synthesis of the MK-5

3,3,3',3',-tetramethyl-spirobisindane-6,6'-dihydroxyl-5,5'-diamine was used as the starting diamine compound and the resulting polyimide (MK-5) was synthesized by the same procedure as MK-1 with a yield of 95%. $^1$H NMR (400 MHz, DMSO-d$_6$): 9.52 (s, 2H), 8.73 (s, 2H), 8.40 (s, 2H), 7.53 (s, 2H), 7.29 (s, 2H), 7.07 (s, 4H), 6.78 (s, 2H), 6.33 (s, 2H), 2.13-2.34 (m, 4H), 1.27 (s, 12H); Molecular weight (GPC in chloroform) $M_n=6.73\times10^4$; $M_w=10.1\times10^4$; PDI=1.50.

Example 8

Synthesis of the MK-6

9,9'-spirobifluorene-2,2'-dihydroxyl-3,3'-diamine was used as the starting diamine compound and the resulting polyimide (MK-6) was synthesized by the same procedure as MK-1 with a yield of 95%. $^1$H NMR (400 MHz, CDCl$_3$): 9.89 (s, 2H), 8.80 (s, 2H), 8.41 (s, 2H), 7.77-7.88 (m, 4H), 7.54 (s, 2H), 7.13-7.32 (m, 8H), 6.67-6.80 (m, 4H), 6.20 (s, 2H); Molecular weight (GPC in chloroform) $M_n=6.38\times10^4$; $M_w=11.7\times10^4$; PDI=1.84.

TABLE 1

Solubility of the polyimides

| Polymers | m-Cresol | NMP | DMF | THF | CHCl$_3$ | Acetone | MeOH |
|---|---|---|---|---|---|---|---|
| MK-1 | + | -- | -- | -- | ++ | -- | -- |
| MK-2 | +- | +- | -- | -- | ++ | -- | -- |
| MK-3 | ++ | ++ | ++ | + | ++ | -- | -- |
| MK-4 | ++ | ++ | ++ | ++ | ++ | +- | -- |
| MK-5 | ++ | ++ | ++ | ++ | -- | +- | -- |
| MK-6 | ++ | ++ | ++ | ++ | -- | +- | -- |

++ Solubility over 5 mg/mL; +– Solubility between 1 mg/mL and 5 mg/mL, --: solubility smaller than 1 mg/mL.

TABLE 2

BET Surface area and other properties of the novel polymers

| Polymers | MK-1 | MK-2 | MK-3 | MK-4 | MK-5 | MK-6 |
|---|---|---|---|---|---|---|
| BET surface area (m$^2$/g) | 754 | 782 | 500 | 420 | 470 | 460 |

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim at least the following:
1. A composition, comprising:
an aromatic dianhydride having the following structure:

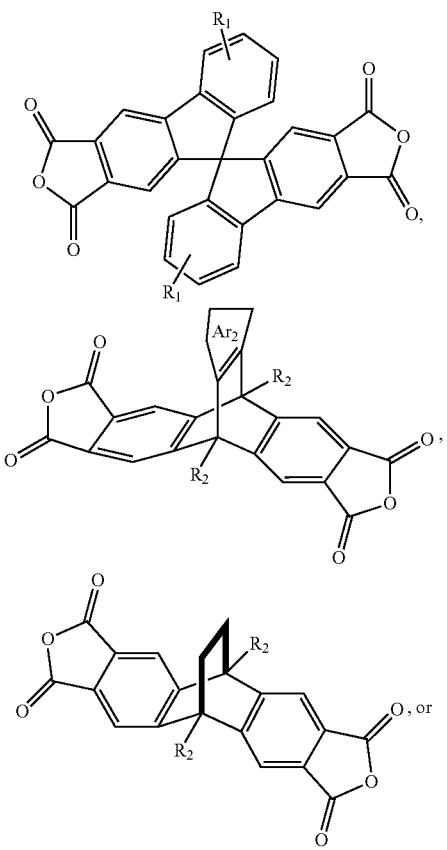

-continued

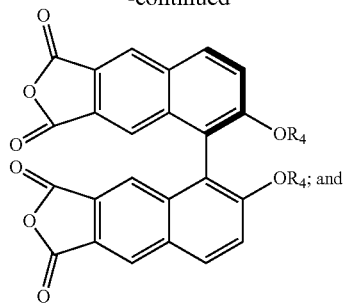

wherein each R₁, R₂, and R₄ are independently selected from the group consisting of: a linear or branched, substituted or unsubstituted, alkyl group, wherein Ar₂ is selected from the group consisting of: an aryl group, a polyaromatic group, and a heteroaryl group where each are substituted or unsubstituted.

2. The composition of claim 1, wherein Ar₂ is selected from:

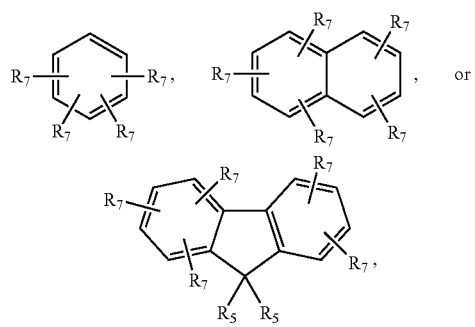

substituted or unsubstituted, and wherein R₅ and R₇ are independently selected from a linear or branched, substituted or unsubstituted, alkyl group.

3. A composition, comprising:
a polymide having the following structure:

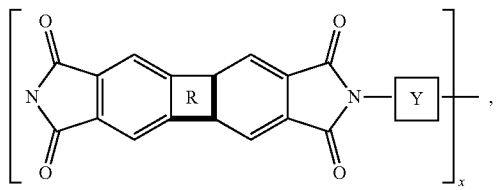

wherein Y is selected from an aryl group a polyaromatic group, or a heteroaryl group, wherein x is 1 to 10,000, wherein R is selected from the following structures:

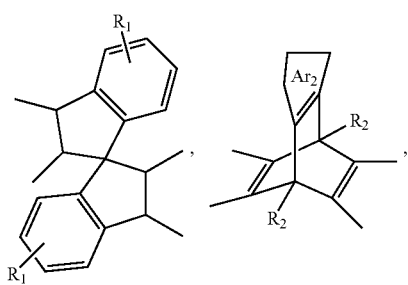

-continued

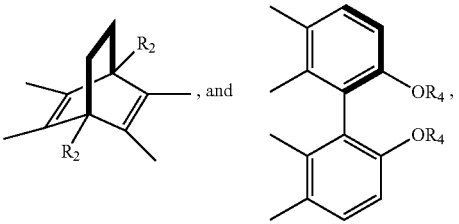

wherein each of R₁, R₂, and R₄ are independently selected from the group consisting of: a linear or branched, substituted or unsubstituted alkyl group, wherein Ar₂ is selected from the group consisting of: an aryl group, a polyaromatic group, and a heteroaryl group where each can be substituted or unsubstituted.

4. A composition, comprising:
a polyimide having the following structure:

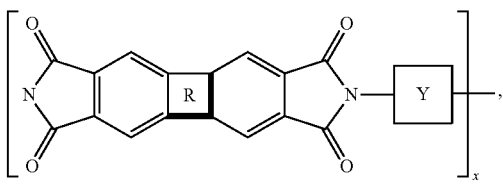

wherein Y is selected from an aryl group a polyaromatic group, or a heteroaryl group, wherein x is 1 to 10,000, wherein R is selected from the following structures:

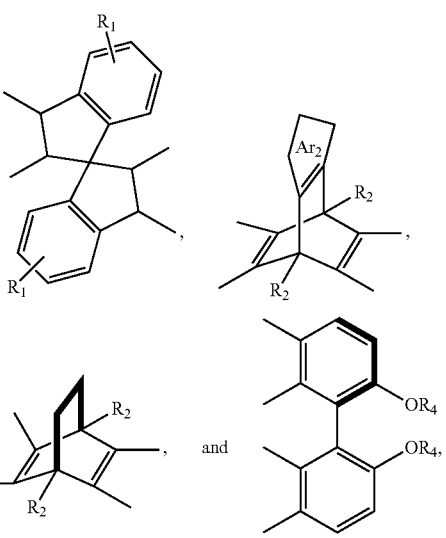

wherein each of $R_1$, $R_2$, and $R_4$ are independently selected from the group consisting of: a linear or branched, substituted or unsubstituted alkyl group, wherein $Ar_2$ is selected from the group consisting of: an aryl group, a polyaromatic group, and a heteroaryl group where each can be substituted or unsubstituted, and
wherein $Ar_2$ is selected from

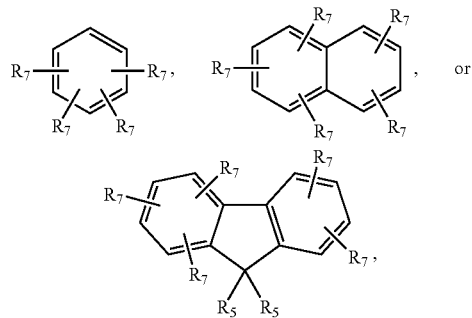

substituted or unsubstituted, and wherein $R_5$ and $R_7$ are independently selected from a linear or branched, substituted or unsubstituted, alkyl group.

5. The composition of claim 3, wherein Y is selected from the group consisting of:

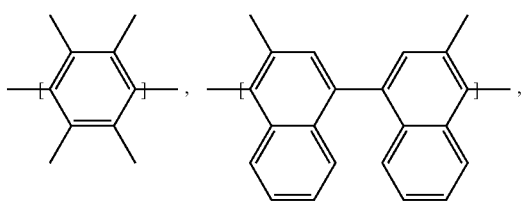

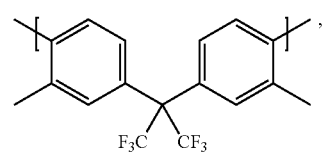

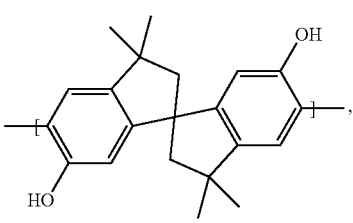

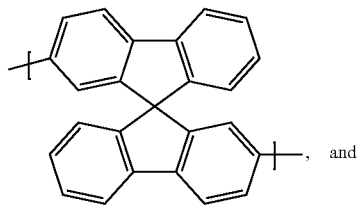

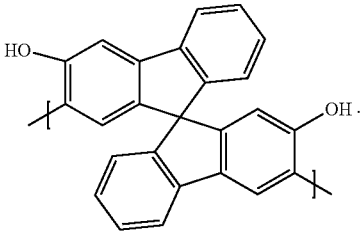

6. A composition, comprising:
a polyimide having the following structure:

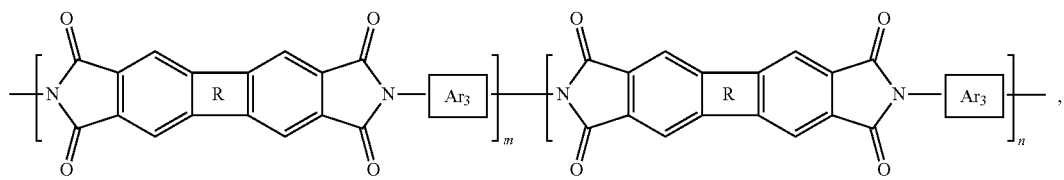

wherein $Ar_3$ and $Ar_4$ are independently selected from an aryl group a polyaromatic group, or a heteroaryl group, wherein m and n are independently 0 to 10,000, wherein R is selected from the following structures:

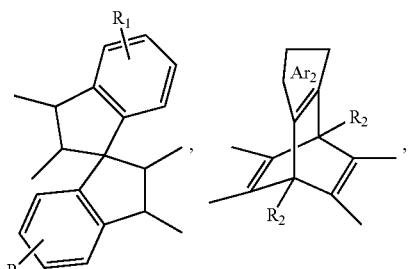

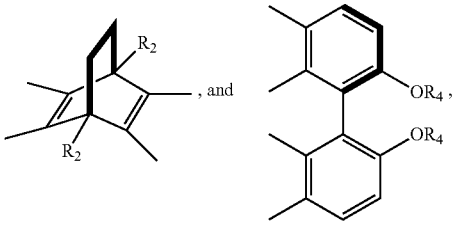

wherein $R_1$, $R_2$, and $R_4$ are independently selected from the group consisting of: a linear or branched, substituted or unsubstituted alkyl group, wherein $Ar_2$ is selected from the group consisting of: an aryl group, a polyaromatic group, and a heteroaryl group, wherein $R_5$ is a linear or branched, substituted or unsubstituted alkyl group.

7. The composition of claim 6, wherein $Ar_3$ and $Ar_4$ are different and m and n are 1 to 10,000.

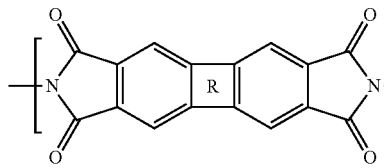

wherein $Ar_3$ and $Ar_4$ are independently selected from an aryl group a polyaromatic group, or a heteroaryl group, wherein m and n are independently 0 or 10,000, wherein R is selected from the following structures:

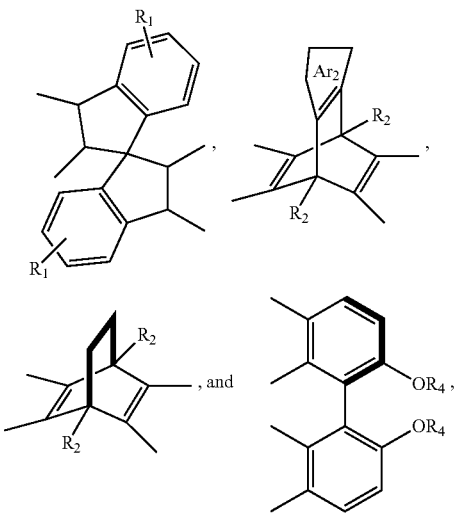

wherein $R_1$, $R_2$, and $R_4$ are independently selected from the group consisting of: a linear or branched, substituted or unsubstituted alkyl group, wherein $Ar_2$ is selected from the group consisting of: an aryl group, a polyaromatic group, and a heteroaryl group, wherein $R_5$ is a linear or branched, substituted or unsubstituted alkyl group, and wherein $Ar_3$ and $Ar_4$ are each independently selected from the group consisting of:

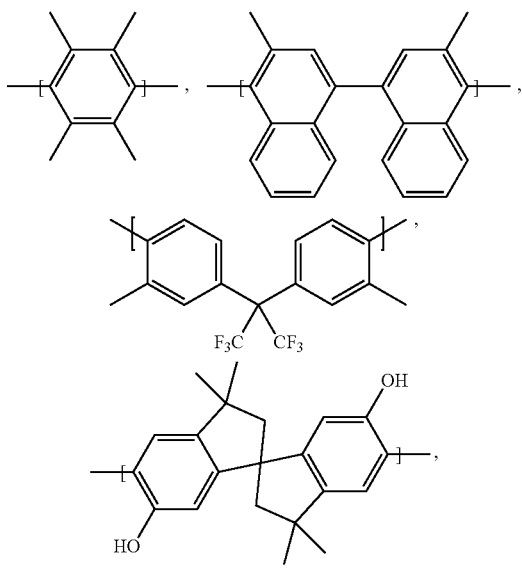

8. A composition, comprising:
a polyimide having the following structure:

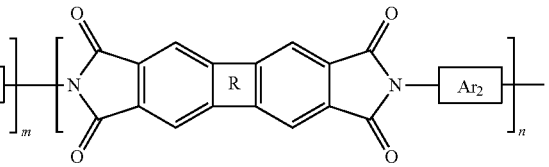

-continued

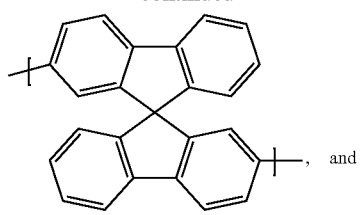
, and

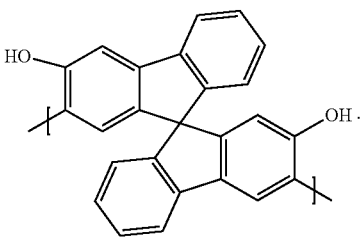

9. A method of making an aromatic dianhydride, comprising:

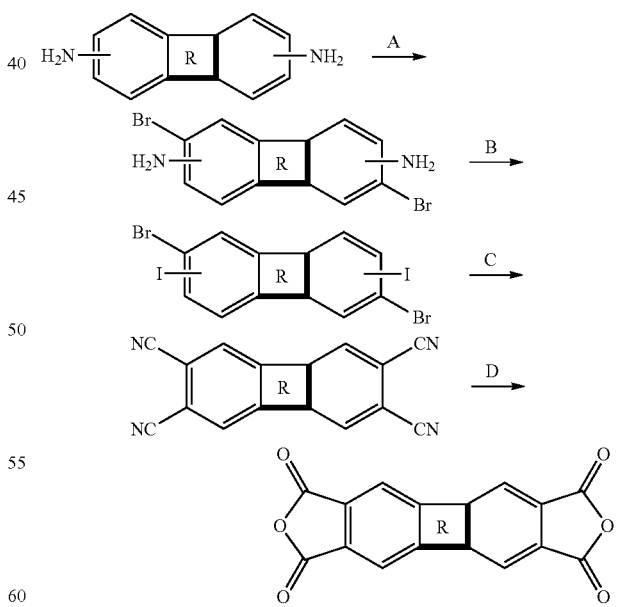

wherein A includes N-bromosuccinimide, wherein B includes sodium nitrite, wherein C includes copper cyanide, wherein D includes potassium hydroxide followed by acetic anhydride, wherein R is selected from the following structures;

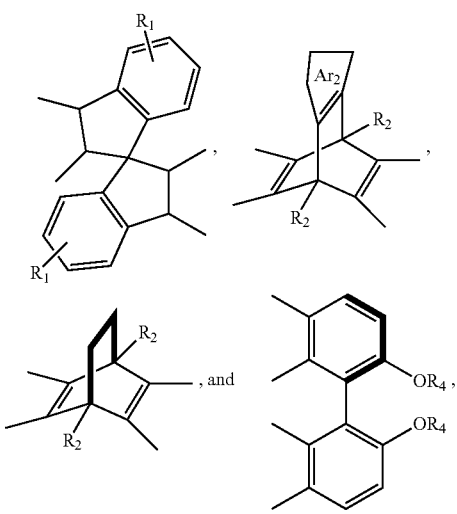

wherein $R_1$, $R_2$, and $R_4$ are independently selected from the group consisting of: a linear or branched, substituted or unsubstituted alkyl group, wherein $Ar_2$ is selected from the group consisting of: an aryl group, a polyaromatic group, and a heteroaryl group where each is substituted or unsubstituted.

10. The method of claim 9, wherein $Ar_2$ is selected from:

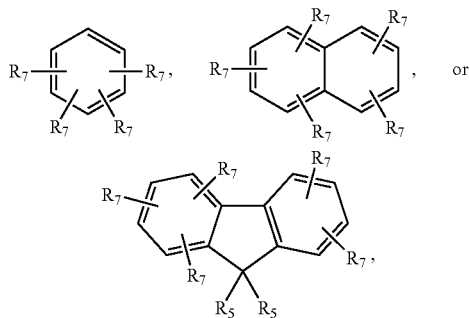

substituted or unsubstituted, and wherein $R_5$ and $R_7$ are independently selected from a linear or branched, substituted or unsubstituted, alkyl group.

11. A method for making a polyimide, comprising: reacting an aromatic dianhydride with a multi-amine to form a polyimide, wherein the aromatic dianhydride has the following structure:

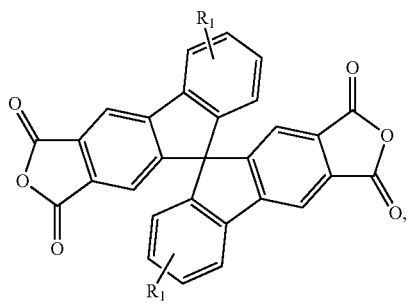

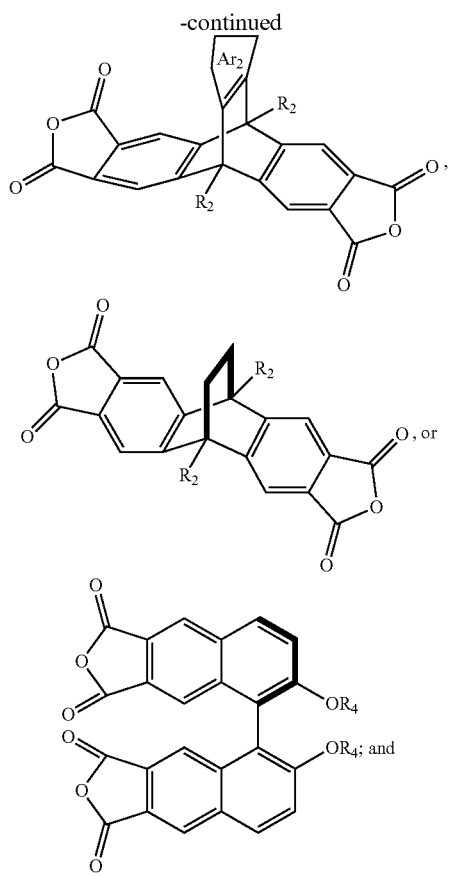

wherein each $R_1$, $R_2$, and $R_4$ are independently selected from the group consisting of: a linear or branched, substituted or unsubstituted, alkyl group, wherein $Ar_2$ is selected from the group consisting of: an aryl group, a polyaromatic group, and a heteroaryl group where each are substituted or unsubstituted.

12. The method of claim 11, wherein the multi-amine is selected from the group consisting of a diamine, a triamine, a tetramine, and an amine having 5 or more amino groups.

13. The method of claim 11, wherein the multiamine is selected from the group consisting of:

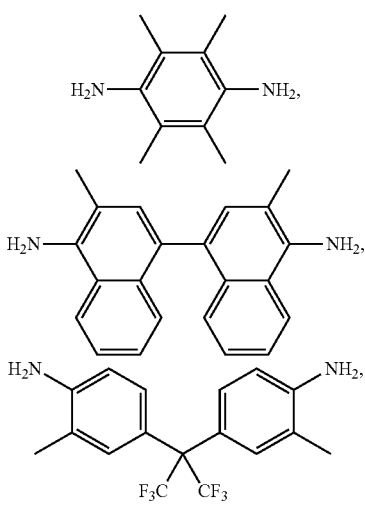

-continued

[Chemical structure: 2,2'-diamino-9,9'-spirobifluorene]

MK-4

[Chemical structure: spirobiindane with amino and hydroxy substituents]

and

[Chemical structure: spirobifluorene with amino and hydroxy substituents]

* * * * *